United States Patent
Mathis et al.

(10) Patent No.: US 6,753,156 B1
(45) Date of Patent: Jun. 22, 2004

(54) HOMOGENEOUS METHOD FOR DETECTING AND/OR DETERMINING PHOSPHORYLATING ACTIVITY IN A BIOLOGICAL MATERIAL

(75) Inventors: Gérard Mathis, Bagnols sur Ceze (FR); Eric Trinquet, Pont Saint Esprit (FR); Marc Preaudat, Connaux (FR)

(73) Assignee: Cis Bio International, Saclay (FR)

( * ) Notice: Subject to any disclaimer, the term of this patent is extended or adjusted under 35 U.S.C. 154(b) by 0 days.

(21) Appl. No.: 09/486,701

(22) PCT Filed: Sep. 16, 1998

(86) PCT No.: PCT/FR98/01976

§ 371 (c)(1),
(2), (4) Date: Mar. 17, 2000

(87) PCT Pub. No.: WO99/15896

PCT Pub. Date: Apr. 1, 1999

(30) Foreign Application Priority Data

Sep. 19, 1997 (FR) .............................................. 97 11721

(51) Int. Cl.⁷ .................... G01N 33/573; G01N 33/533; G01N 33/542
(52) U.S. Cl. ........................ 435/7.4; 435/975; 436/546; 436/537; 436/815; 530/391.3
(58) Field of Search ................................ 436/546, 537, 436/815; 530/391.3; 435/7.4, 975

(56) References Cited

U.S. PATENT DOCUMENTS 5,279,943 A 1/1994 Mathis et al.
5,439,797 A 8/1995 Tsien et al.
5,925,558 A * 7/1999 Tsien et al.
6,203,994 B1 * 3/2001 Epps et al.

FOREIGN PATENT DOCUMENTS

| CA | 1329593 | 5/1994 |
| WO | 93 05049 | 3/1993 |
| WO | 96 00901 | 1/1996 |
| WO | 96 42016 | 12/1996 |
| WO | 98 02571 | 1/1998 |
| WO | 98 09169 | 3/1998 |

OTHER PUBLICATIONS

"Oligomerization of Epidermal Growth . . . Activation", Gadella et al, Journal of Cell Biology 129 (6), 1995, pp. 1543–1558.

"Analysis of C–Kit Receptor Dimerization . . . transfer", Broudy et al, XP002065455, 1998, pp. 898–906.

"Measurement of Distance Between Fluorescent Amino–Acid . . . Thermolysin", Horrocks et al, XP002065456, 1981, pp. 111–117.

* cited by examiner

Primary Examiner—Mary E. Ceperley
(74) Attorney, Agent, or Firm—Millen, White, Zelano & Branigan, P.C.

(57) ABSTRACT

The invention relates to a novel homogeneous method of detecting and/or determining the phosphorylating activity of a biological material towards a substrate containing tyrosine and/or serine and/or threonine, and to a kit for carrying out this method.

21 Claims, 1 Drawing Sheet

HOMOGENEOUS METHOD FOR DETECTING AND/OR DETERMINING PHOSPHORYLATING ACTIVITY IN A BIOLOGICAL MATERIAL

BACKGROUND OF THE INVENTION

The invention relates to a novel homogeneous method of detecting and/or determining the phosphorylating activity of a biological material towards a substrate containing tyrosine and/or serine and/or threonine, and to a kit for carrying out this method.

The phosphorylation of biological molecules, such as peptides or proteins, by kinases is a major biological mechanism for regulating cell metabolism.

The majority of enzymes which possess a phosphorylating activity have a very high Km (Michaelis constant) (generally of between $10^{-3}$ and $10^{-5}$ M) and a very low conversion yield (between 5% and 0.001% of the active sites of the substrate are phosphorylated).

Under these conditions, it is only possible to detect the phosphorylation of a substrate if the active sites are present in large excess during the reaction. This large excess of active sites can be obtained either by using high concentrations of substrate (if it only has a few active sites) or by choosing a substrate which possesses a large number of phosphorylation sites.

To date, the mechanisms of phosphorylation have generally been studied by radioactive or enzymatic heterogeneous methods of detection.

In methods of this type, the phosphorylation of the substrate fixed to a solid phase is detected either by measuring the incorporation of $^{32}P$ into the enzyme substrate or by using a labeled antibody (isotopic, enzymatic or fluorescent tracer) directed against the phosphorylation site.

This type of assay makes it possible to fix a large amount of substrate to the solid phase and hence to detect the phosphorylation even when the substrate possesses only a small number of active sites, but it nevertheless has major disadvantages, namely:

the frequent use of isotopic markers, the need for separation processes between the different steps of the assay in order to remove the excess reagents, and the need to control the substrate "capture" processes (for example when using a plate carrying avidin with a biotin substrate).

In the case of a homogeneous method, it is often necessary for the concentration of the substrate to be high in order to generate a sufficient amount of phosphorylated substrate to detect. It then becomes difficult to capture all the substrate as this would require a large amount of reagent, which, if the reagent is fluorescent, has the disadvantage of generating a high specific background noise.

SUMMARY OF THE INVENTION

It has now been found that the phosphorylation of a substrate can be detected by means of a homogeneous method using a luminescent carrier molecule to which a plurality of substrates are covalently coupled. After the enzymatic phosphorylation reaction, the amount of phosphorylated substrate is disclosed by measuring the signal emitted by the luminescent carrier molecule and generated by energy transfer from a specific receptor for the phosphorylated substrate labeled with a luminescent molecule.

This method is particularly useful for measuring the phosphorylation of molecules of biological interest, for example peptides, polypeptides, proteins or nucleotides, in natural or pathological processes, or in synthetic processes such as the synthesis of nucleic acids or proteins.

DETAILED DESCRIPTION OF THE INVENTION

Figure 1:
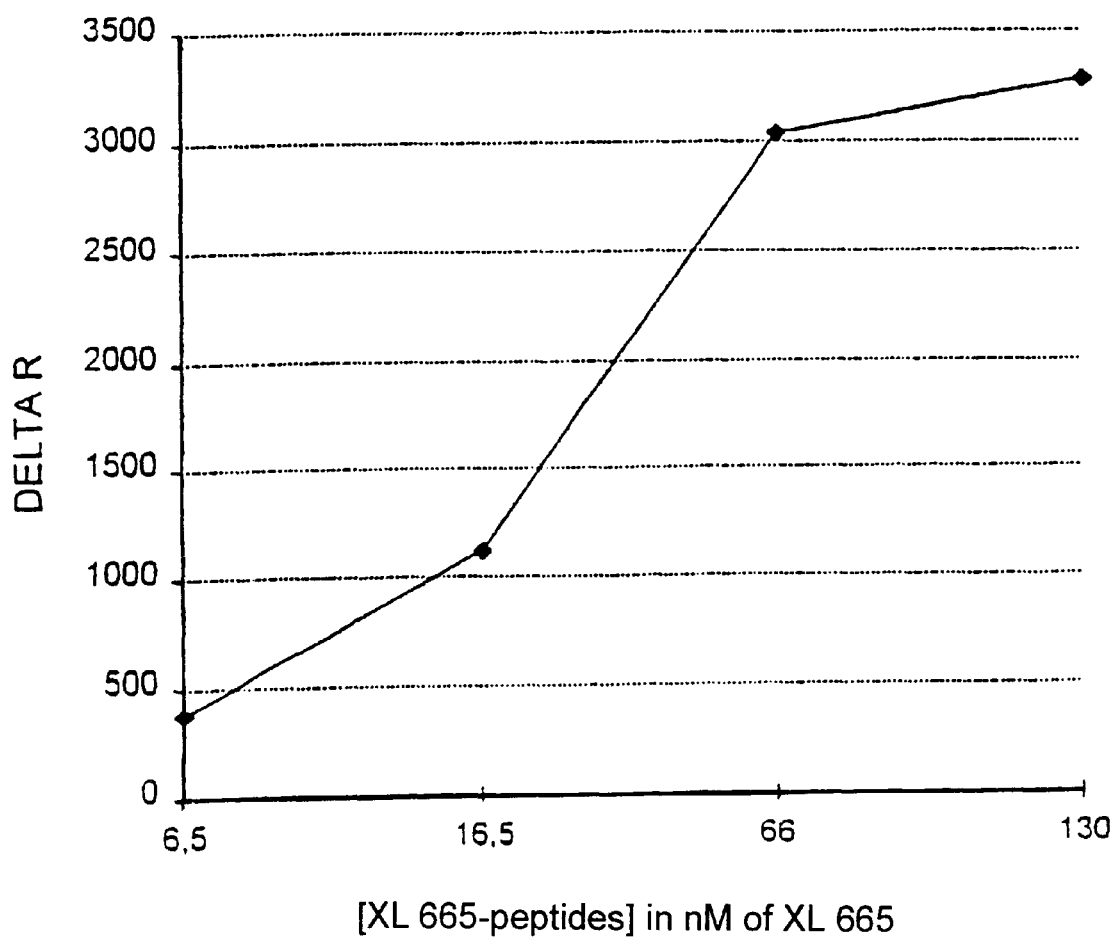
FIG. 1 illustrates degree of phosphorylation in an exemplary assay.

According to a first feature, the invention therefore relates to a homogeneous method of detecting and/or determining the phosphorylating activity of a biological material towards a substrate containing tyrosine and/or serine and/or threonine, characterized in that said biological material is brought into contact with a plurality of identical or different peptides or polypeptides containing tyrosine and/or serine and/or threonine, covalently bonded to a carrier molecule, in the presence of a source of non-radiolabeled phosphate and specific receptors for said phosphorylated peptides or polypeptides, and in that the phosphorylating activity is detected and/or determined by measuring an emission signal, said emission signal resulting from an interaction between said carrier molecule, consisting of a luminescent molecule or a non-luminescent molecule bonded to at least one luminescent marker or at least one emission signal modulator, and said specific receptors bonded to at least one luminescent marker or at least one emission signal modulator.

"Luminescent marker" is understood as meaning a luminescent molecule used to detect the interaction between the carrier molecule and the specific receptor.

"Emission signal modulator" is understood as meaning a molecule which, when situated near a luminescent molecule, modifies the characteristics of the emission signal of said luminescent molecule.

Depending on the molecules used respectively as the carrier molecule and as the specific receptor, and depending on the mechanism of their interaction, one and the same luminescent compound can act as a luminescent marker or as an emission signal modulator.

Said modulator can be a luminescent molecule, for example a luminescent donor or acceptor molecule, or a non-luminescent molecule, for example an atom of high atomic number or a molecule containing such an atom, as described for example in patent application EP 0 232 348, or a spin marker.

The carrier molecule can be:

either a luminescent molecule with a high molecular weight in the order of several tens of kdaltons, for example a fluorescent molecule such as allophycocyanin or C phycocyanin;

or a non-luminescent molecule, for example thyroglobulin, bonded to at least one luminescent marker or at least one emission signal modulator;

or a luminescent dispersed solid with a sufficient surface area to fix a plurality of peptide or polypeptide substrates;

or a non-luminescent dispersed solid with a sufficient surface area to fix a plurality of peptide or polypeptide substrates, bonded to at least one luminescent marker or at least one emission signal modulator.

The carrier molecule can therefore be either a luminescent acceptor molecule or a non-luminescent molecule bonded to at least one luminescent marker or at least one emission signal modulator.

In the remainder of the description, the terms "molecule" and "compound" will be used indiscriminately to qualify the luminescent markers or the modulators bonded to the carrier molecule or the specific receptor.

According to one advantageous feature, the carrier molecule is either a fluorescent acceptor molecule, or a fluorescent donor molecule, or a non-fluorescent molecule bonded to at least one fluorescent acceptor compound or at least one fluorescent donor compound.

Advantageously, the luminescent marker or the emission signal modulator bonded to each of the specific receptors for the phosphorylated peptide(s) or polypeptide(s) can be a fluorescent donor or acceptor molecule.

According to one preferred feature, the phosphorylating activity is detected and/or determined by measuring the emission signal resulting from the non-radiative energy transfer between the carrier molecule and the luminescent markers or the emission signal modulators bonded to the specific receptors for the phosphorylated peptides or polypeptides.

Thus the luminous emission signal which allows the desired detection and/or determination of the phosphorylating activity can be generated either by non-radiative energy transfer to the carrier molecule from the luminescent markers or the emission signal modulators bonded to the specific receptors, or, conversely, by non-radiative energy transfer from the luminescent markers or the emission signal modulators of the carrier molecule to the luminescent markers bonded to the specific receptors.

"Energy transfer between the carrier molecule and the luminescent marker molecules or the emission signal modulators bonded to the specific receptors for the phosphorylated peptides or polypeptides" is therefore understood as meaning the 2 types of mechanism mentioned above.

Non-radiative energy transfer, the principle of which is described particularly in G. Mathis et al., Clin. Chem., 1993, 39, 1953–1959, takes place when the following conditions are fulfilled:

- on the one hand, the acceptor compound possesses an absorption spectrum which at least partially overlaps the emission spectrum of the donor and has a high molar absorbance in this overlap zone, and an emission spectrum over a wavelength range in which the donor has a weak intrinsic emission;
- on the other hand, the acceptor and the donor are situated near one another.

The amount of peptides or polypeptides covalently bonded to the luminescent carrier molecule can be about 2 to 1000 per luminescent carrier molecule.

The specific receptors for the phosphorylated peptides or polypeptides can be selected for example from monoclonal and polyclonal antibodies.

According to one preferred feature, the luminescent compound bonded to the specific receptor for the phosphorylated peptide(s) or polypeptide(s) or to the carrier molecule as a luminescent marker or an emission signal modulator, depending on the mechanism of interaction between said carrier molecule and said specific receptor, is a chelate, a cryptate or a macrocyclic complex of a rare earth ion.

In the remainder of the description, the terms "chelate" and "cryptate" and the nomenclature of the macrocycles and polycycles which can be used are as defined by J. M. Lehn in Struct. Bonding (Berlin), 16, 1, 1973 and in Acc. Chem. Res., 11, 49 (1979).

Said fluorescent donor compound is preferably a rare earth cryptate selected from terbium, europium, samarium (ineodyminum) and dysprosium cryptates.

According to one preferred feature, said rare earth cryptate consists of at least one rare earth salt complexed by a macropolycyclic compound of the formula

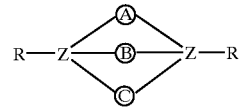

I in which Z is a trivalent or tetravalent atom, R is nothing, hydrogen, the hydroxyl group, an amino group or a hydrocarbon radical, and the divalent radicals Ⓐ, Ⓑ and Ⓒ independently of one another are hydrocarbon chains which optionally contain one or more heteroatoms and are optionally interrupted by a heteromacrocycle, at least one of the radicals Ⓐ, Ⓑ and Ⓒ also containing at least one molecular moiety or essentially consisting of a molecular moiety, said molecular moiety possessing a greater triplet energy than that of the emission level of the complexed rare earth ion.

Said cryptate is preferably a cryptate of formula (I) above in which the molecular moiety is selected from phenanthroline, anthracene, benzene, naphthalene, bi- and ter-phenyl, azobenzene, azopyridine, pyridine, bipyridines, bis-quinolines and compounds of the following formulae:

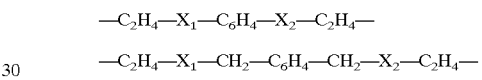

$X_1$ and $X_2$, which can be identical or different, denoting oxygen, nitrogen or sulfur,

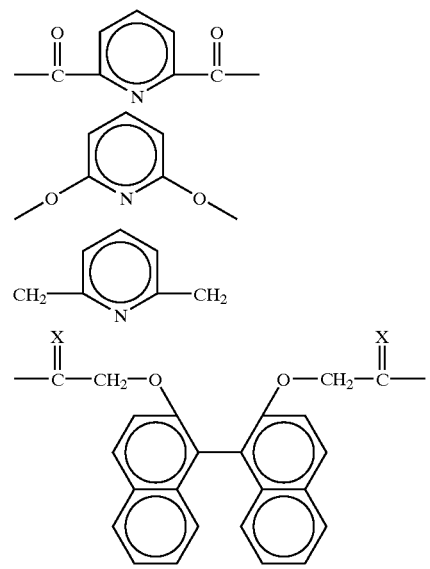

X being oxygen or hydrogen.

According to one advantageous feature, the fluorescent compound is a rare earth cryptate consisting of the terbium or europium ion complexed by one of the following macrocyclic compounds: (22)phenanthroline; (22) phenanthroline amide; (22)anthracene; (22)anthracene amide; (22)biisoquinoline; (22)biphenyl-bis-pyridine; (22) bipyridine; (22)bipyridine amide; and tris-bipyridine, tris-phenanthroline, phenanthroline-bis-bipyridine, biisoquinoline-bis-bipyridine and bis-bipyridine diphenylbipyridine macropolycycles.

One particularly advantageous fluorescent compound is the europium cryptate Eu tris-bipyridine.

Such compounds are described for example in patent EP 180 492.

It is also possible to use macrocyclic compounds which complex rare earth ions and in which the molecular moiety is selected from bipyrazines, bipyrimidines and nitrogen heterocycles containing N-oxide groups.

Macrocyclic compounds containing bipyrazine units are described in F. Bodar-Houillon et al., New J. Chem., 1996, 20, 1041–1045.

Macrocyclic compounds containing bipyrimidine units are described in J. M. Lehn et al., Helv. Chim. Acta, 1992, 75, 1221.

Macrocyclic compounds which comprise nitrogen heterocycles containing N-oxide groups are described in J. M. Lehn et al., Helv. Chim. Acta, 1991, 74, 572 and in patent EP 0 601 113.

The rare earth cryptate used as a fluorescent donor compound can also consist of at least one rare earth salt complexed by a macropolycyclic compound of formula II or III below:

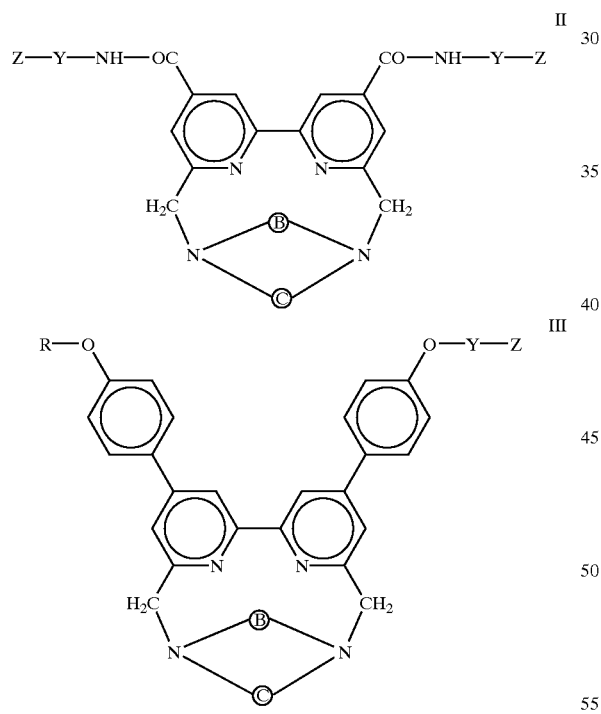

in which:

the ring of the formula

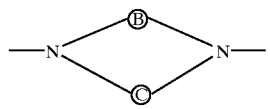

is one of the following rings:

1)

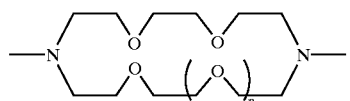

n = 0 or 1
[$N_2O_4$] macrocycle or cycle (22)
[$N_2O_3$] macrocycle or cycle (21)

2)

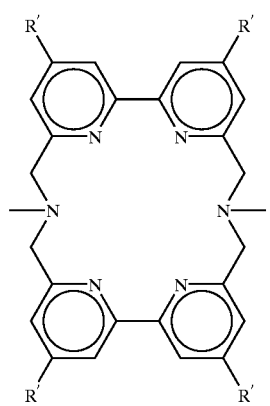

(bis-bipyridine) macrocycle

Y is a group or spacer arm consisting of a divalent organic radical selected from linear or branched $C_1$ to $C_{20}$ alkylene groups optionally containing one or more double bonds or triple bonds and/or optionally being interrupted by one or more heteroatoms such as oxygen, nitrogen, sulfur or phosphorus, from $C_5$ to $C_8$ cycloalkylene groups or from $C_6$ to $C_{14}$ arylene groups, said alkylene, cycloalkylene or arylene groups optionally being substituted by alkyl, aryl or sulfonate groups;

Z is a functional group capable of bonding covalently with a biological substance;

R is a methyl group or the group —Y—Z; and

R' is hydrogen or a group —COOR", in which R" is a $C_1$ to $C_{10}$ alkyl group, preferably the methyl, ethyl or tert-butyl group, or R' is a group —CO—NH—Y—Z.

Such compounds are described for example in patent EP 321 353.

In the method according to the invention, said fluorescent compound can be bonded to the specific receptor or the carrier molecule either directly or via a spacer arm.

This spacer arm consists for example of a divalent organic radical selected from linear or branched $C_1$–$C_{20}$ alkylene groups optionally containing one or more double bonds and/or optionally interrupted by one or more heteroatoms such as oxygen, nitrogen, sulfur or phosphorus; carbamoyl and carboxamido groups; $C_5$–$C_8$ cycloalkylene groups; and $C_6$–$C_{14}$ arylene groups, said alkylene, cycloalkylene or arylene groups optionally being substituted by alkyl, aryl or sulfonate groups.

According to one preferred feature, a europium cryptate will be used as a fluorescent donor compound bonded to the specific receptor, and allophycocyanin, allophycocyanin B, a chemically modified allophycocyanin derivative, C phycocyanin, R phycocyanin or a cyanin will be used as a carrier molecule or a fluorescent acceptor compound bonded to the carrier molecule.

According to another advantageous feature, a terbium cryptate will be used as a fluorescent donor compound bonded to the specific receptor, and a rhodamine, thionine, R phycocyanin, phycoerythrocyanin, C phycoerythrin, B phycoerythrin, R phycoerythrin or a cyanin will be used as a carrier molecule or a fluorescent acceptor molecule bonded to the carrier molecule.

Other fluorescent compounds which can be used as acceptor compounds are the phycobiliprotein/binding peptide complexes described in patent application WO96/42016.

According to another of its features, the invention further relates to a kit for detecting and/or determining the phosphorylating activity of a biological material towards a substrate containing and/or serine and/or threonine, characterized in that it contains at least one carrier molecule to which a plurality of identical or different peptides or polypeptides are covalently fixed, and at least one specific receptor for said phosphorylated peptides or polypeptides, said receptor being bonded to at least one luminescent marker or at least one emission signal modulator.

The carrier molecule is as defined above, i.e. it can be intrinsically luminescent or luminescent by bonding to at least one luminescent marker or at least one emission signal modulator.

Advantageously, the carrier molecule and the luminescent marker or the emission signal modulator bonded to the specific receptor in this kit are fluorescent compounds.

According to one preferred feature, the luminescent compound (luminescent marker or emission signal modulator) bonded to the specific receptor, and the carrier molecule, are respectively fluorescent donor and acceptor compounds.

The luminescent compound bonded to the specific receptor in the kit according to the invention can be the europium cryptate Eu tris-bipyridine or the terbium cryptate Tb tris-bipyridine.

Advantageously, the kit according to the invention also contains an appropriate buffer medium, a source of non-radiolabeled phosphate and instructions for carrying out the above-described method of detecting and/or determining the phosphorylating activity of a biological material.

The invention is illustrated by the Example which follows.

EXAMPLE 1

Detection of the Phosphorylation of SRC Peptide

SRC peptide is a substrate for tyrosine kinase in the receptor of epidermal growth factor, or EGF. It is a peptide of 11 amino acids containing a single tyrosine moiety and having the following structure:

[H]-Leu-Ile-Glu-Asp-Ala-Glu-Tyr-Ala-Ala-Gly-[OH]

The following abbreviations are used below:
DTT=dithiothreitol
EuTBP=the europium cryptate Eu tris-bipyridinediamine
BSA=bovine serum albumin
IgG=immunoglobulin G
MHS=maleimidohexanoyl-N-hydroxysuccinimide ester
SPDP=N-succinimidyl 3-(2-pyridyldithio)propionate
Sulfo-SMCC=sulfosuccinimidyl-[4(N-maleimidomethyl)]cyclohexane
1) Conjugation of the Luminescent Carrier Molecule with the Peptide Substrate A chemically modified allophycocyanin derivative ($XL_{665}$, Cis bio international) is used, the high molecular weight of which allows it to be labeled with numerous peptides each possessing a phosphorylation site.

a) Activation of $XL_{665}$ with SPDP

An 80 mM solution of SPDP in absolute ethanol is added to 6 mg of $XL_{665}$ at a concentration of 3.45 mg/ml in a 100 mM phosphate buffer, pH 7.0, in a (proportion) of 60 mol of activator per mol of $XL_{665}$.

After an activation time of 30 minutes at room temperature, a 200 mM solution of DTT in a 100 mM phosphate buffer, pH 7.0, is added in a proportion of 5 mol of reducing agent per mol of activator.

After 15 minutes at room temperature, the unwanted reaction products are removed by exclusion-diffusion chromatography on a superfine G25 gel column in a 100 mM phosphate buffer, pH 6.5, 5 mM EDTA.

The product is stored at 4° C. before coupling.

b) Activation of the Peptide with MHS

A 220 mM solution of MHS in acetonitrile is added to 4 mg of peptide (2.6 pmol) in a proportion of 4 mol of activator per mol of peptide.

After 30 minutes at room temperature, the unwanted reaction products are removed by exclusion-diffusion chromatography on a Superdex 30 gel column (PHARMACIA) in a 100 mM phosphate buffer, pH 7.0.

c) Peptide-maleimide/$XL_{665}$-SH Coupling

In a manner similar to that described above, the maleimide groups are reacted with the thiol groups fixed to the $XL_{665}$, in a molar proportion of 100 peptides per $XL_{665}$.

After incubation for 18 hours at 40° C. and blocking of any free thiol groups remaining with N-ethylmaleimide, the non-coupled peptide is removed by exclusion-diffusion chromatography on a TSK 3000 SW column (MERCK) in a 100 mM phosphate buffer, pH 7.0.

This gives a conjugate containing between 20 and 40 peptides per $XL_{665}$ molecule.

2) Preparation of the Conjugate Between Anti-phosphotyrosine Antibody and the Europium Cryptate Eu Tris-bipyridine a) Activation of IgG PY20 with SPDP 5 mg of IgG PY20 (Transduction Laboratories) at a concentration of 10 mg/ml in a 100 mM phosphate buffer, pH 7.0, are activated by the addition of a solution of SPDP (Pierce, USA) at a concentration of 6.4 mM in dioxane, in a molar ratio of 7.5 SPDP per IgG PY20.

After an activation time of 35 min at room temperature, the IgG pyridine-2-thione is purified on a superfine G25 column in a 100 mM phosphate buffer, 5 mM EDTA, pH 6.5.

The proteins are concentrated and the 2-pyridyl disulfide groups are reduced with a solution of DTT (Sigma, USA) having a final concentration of 19 mM, for 15 min at room temperature. The DTT and the pyridine-2-thione are removed by purification on a superfine G25 column in a 100 mM phosphate buffer, 5 mM EDTA, pH 6.5. The concentration of IgG-SH is determined at 280 nm with an $\epsilon_{280\,nm}$ of 210,000 $M^{-1}$ $cm^{-1}$.

b) Preparation of the IgG PY20/EuTBP Conjugates

A 25 mM solution of sulfo-SMCC in a 20 mM phosphate buffer, 10% dimethylformamide (v/v, pH 7.0), is added to 5 mg ($5.10^{-6}$ mol) of EuTBP (the europium cryptate Eu tris-bipyridinediamine prepared as described in patent EP 321 353, Examples 3 and 4) in a proportion of 2.5 mol of activator per mol of EuTBP.

After an activation time of 45 min at room temperature, the reaction medium is filtered through a 0.8 μm filter to remove any precipitate formed. The unwanted reaction products (sulfo-SMCC, N-hydroxysuccinimide, (N-maleimidomethyl)carboxylic acid) are removed by ion exchange chromatography on a Mono Q column (Pharmacia, Sweden) in a 20 mM phosphate buffer, 10% dimethylformamide (v/v), pH 7.0, under NaCl shock. The concentration of EuTBP-maleimide is determined at 307 nm with an $\epsilon_{307\ nm}$ of 25,000 $M^{-1}$ $cm^{-1}$, and the ratio $A_{307\ nm}/A_{280\ nm}$ is also determined.

In a manner similar to that described above, the maleimide groups are reacted with the thiol groups fixed to the antibody, in molar proportions varying from 10 to 30 EuTBP-maleimide per IgG PY20-SH.

After incubation for 18 hours at 4° C. and blocking of any free thiol groups remaining with N-ethylmaleimide, the non-coupled EuTBP is removed by dialysis in a 100 mM phosphate buffer, pH 7.0, at 4° C. to the point of exhaustion (no further fluorescence in the dialysis baths).

The characteristics of the conjugate are determined by its absorptions at 307 nm and 280 nm using the following values, allowing for the intrinsic absorption of the cryptate determined by the ratio $A_{307\ nm}/A_{280\ nm}$.

EuTBP-maleimide:

$\epsilon_{307\ nm}$=25,000 $M^{-1}$ $cm^{-1}$ $A_{307\ nm}/A_{280\ nm}$=determined experimentally IgG PY20-SH:

$\epsilon_{280\ nm}$=210,000 $M^{-1}$ $cm^{-1}$

3) Phosphorylation

A431 cells (SIGMA) containing an EGF receptor are preactivated with EGF for 10 min at room temperature. The phosphorylation buffer is a 60 mM TRIS/MES buffer, pH 7.4, containing 30 µM ATP, 50 mM $Mg^{++}$ and 10 mM $Mn^{++}$.

The following are added successively to the "assay" wells of a 96-well microplate:

10 µl of preactivated A431 cells

10 µl of $XL_{665}$/SRC peptide conjugate

30 µl of phosphorylation buffer

10 µl of $XL_{665}$/peptide conjugate and 40 µl of phosphorylation buffer are introduced into the "blank" control wells. This is followed by incubation for 30 min at room temperature.

4) Disclosure

The following are added successively to each microplate well:

50 µl of anti-phosphotyrosine antibody labeled with the cryptate Eu tris-bipyridine 100 µl of a 0.1 M phosphate buffer, pH 7, 0.4 M KF, 0.1% BSA After incubation for 30 min at room temperature, the fluorescence is read off at 620 nm and 665 nm by means of the prototype laser fluorimeter described below:

A nitrogen pulsed laser (LASER SCIENCE INC., model LS1-337ND) is used as the excitation source (wavelength at 337.1 nm). The specified pulse duration is 3 nanoseconds and is repeated at a frequency of 10 Hertz. The beam passes through a filter (CORNING) to remove any light, other than 337 nm, interfering with the excitation.

After entering the measurement chamber, the beam is reflected by a dichroic filter placed at 45 degrees, which has the property of reflecting ultraviolet and transmitting visible light.

The beam reflected by the dichroic filter is focused by a fused silica lens onto the microplate well to be measured. The fluorescence emission is collected at a solid angle of 20 degrees, is collimated by the same lens and passes directly through the dichroic filter (visible light fluorescence).

An interference filter, with characteristics defined according to the fluorescence wavelength to be detected, makes it possible to remove the light capable of interfering with the signal, the intensity of which is then measured by a photomultiplier (HAMAMATSU R2949).

The photon counter used is an SR-400 (STANFORD RESEARCH SYSTEMS) whose operations and synchronization with the laser are controlled by an IBM PC-AT computer via an RS232 port. The pulses produced by the photo-multiplier are recorded over a given time window ($t_g$) and after a given delay ($t_d$) provided they are above a discrimination level selected by the photon counter so as to optimize the signal-to-noise ratio of the photomultiplier.

An X-Y plotter, driven by the IBM PC-AT, makes it possible to obtain the different positions of the measurement microplate by means of stepping motors, including the maneuvers of loading, positioning underneath the exciting beam, automatic sequential reading of the 96 wells, and exit.

The fluorescence emitted by the $XL_{665}$/SRC peptide conjugate is measured by means of the prototype fluorimeter equipped with a 665 nm filter (width at half-height: 10 nm), over 400 µs and with a delay of 50 µs.

The results are given on the graph of FIG. 1, in which the ordinate shows the degree of phosphorylation and the abscissa shows the concentration of $XL_{665}$/SRC peptide conjugate.

The degree of phosphorylation is expressed by the variable $DR=R_{sample}-R_{blank}$, R being the ratio of the emission signals at 665 nm and 620 nm.

The concentration of $XL_{665}$/SRC peptide conjugate is expressed in nM of $XL_{665}$.

The results show that the increase in the degree of phosphorylation correlates with the increase in the concentration of $XL_{665}$/SRC peptide conjugate.

What is claimed is:

1. A homogeneous method for detecting and/or determining the phosphorylating activity of a biological material towards a substrate containing tyrosine and/or serine and/or threonine, comprising bringing said biological material into contact with a plurality of identical or different peptides or polypeptides containing tyrosine and/or serine and/or threonine, covalently bonded to a carrier molecule, in the presence of a source of non-radiolabeled phosphate and specific receptors for said phosphorylated peptides or polypeptides, and detecting phosphorylating activity by measuring an emission signal, said emission signal resulting from an interaction between said carrier molecule, consisting of a luminescent molecule or a non-luminescent molecule bonded to at least one luminescent marker or at least one emission signal modulator, and said specific receptors bonded to at least one luminescent marker or at least one emission signal modulator.

2. The method according to claim 1, wherein the phosphorylating activity is detected and/or determined by measuring the emission signal resulting from the energy transfer between the carrier molecule and the luminescent marker or the emission signal modulator bonded to the specific receptors for the phosphorylated peptides or polypeptides.

3. The method according to claim 1, wherein the carrier molecule is a fluorescent molecule or a non-fluorescent molecule bonded to at least one fluorescent marker or at least one emission signal modulator.

4. The method according to claim 1, wherein the luminescent marker or the emission signal modulator bonded to the specific receptor is a fluorescent compound.

5. The method according to claim 1, wherein the specific receptor is bonded to a fluorescent donor compound and the carrier molecule is a fluorescent acceptor molecule or is bonded to a fluorescent acceptor compound.

6. The method according to claim 1, wherein the specific receptor is bonded to a fluorescent acceptor compound and the luminescent carrier molecule is a fluorescent donor molecule or is bonded to a fluorescent donor compound.

7. The method according to claim 1, wherein the amount of peptides or polypeptides covalently bonded to the luminescent carrier molecule is 2 to 1000.

8. The method according to claim 1, wherein the specific receptor is bonded to a chelate, a cryptate or a macrocyclic compled of a rare earth ion.

9. The method according to claim 8, wherein the specific receptor is bonded to a chelate, a cryptate or a macrocyclic complex of europium, terbium, dysprosium, samarium or neodymium.

10. The method according to claim 9, wherein the specific receptor is bonded to a rare earth cryptate consisting of at least one rare earth salt complexed by a macropolycyclic compound of the formula

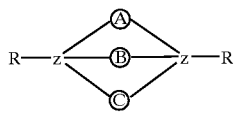 (I)

in which Z is a trivalent or tetravalent atom, R is nothing, hydrogen, the hydroxyl group, an amino group or a hydrocarbon radical, and the divalent radicals Ⓐ Ⓑ and Ⓒ independently of one another are hydrocarbon chains which optionally contain one or more heteroatoms and are interrupted by a heteromacrocycle, at least one of the radicals Ⓐ Ⓑ and Ⓒ also containing at least one molecular moiety or essentially consisting of a molecular moiety, said molecular moiety possessing a greater triplet energy than that of the emission level of the complexed rare earth ion.

11. The method according to claim 10, wherein the fluorescent compound bonded to the specific receptor is a rare earth cryptate consisting of the terbium or europium ion complexed by one of the following macrocyclic compounds:

(22) phenanthroline; (22) phenanthroline amide; (22) anthracene; (22) anthracene amide; (22) biisoquinoline; (22) biphenyl-bis-pyridine; (22) bipyridine; (22) bipyridine amide; and tris-bipyridine, tris-phenanthroline, phenanthroline-bis-bipyridine, biisoquinoline-bis-bipyridine and bis-bipyridine diphenylbipyridine macropolycycles.

12. The method according to claim 11, wherein said fluorescent compound is the europium cryptate Eu tris-bipyridine.

13. The method according to claim 1, wherein a europium cryptate is used as a fluorescent donor compound bonded to the specific receptor, and allophycocyanin, allophycocyanin B, a chemically modified allophycocyanin derivative, C phycocyanin, R phycocyanin or a cyanin is used as a carrier molecule or a fluorescent acceptor compound bonded to the carrier molecule.

14. The method according to claim 1, wherein a terbium cryptate is used as a fluorescent donor compound bonded to the specific receptor, and a rhodamine, thionine, R phycocyanin, phycoerythrocyanin, C phycoerythrin, B phycoerythrin, R phycoerythrin or a cyanin is used as a carrier molecule or a fluorescent acceptor compound bonded to the carrier molecule.

15. The method according to claim 1, wherein the fluorescent donor compound bonded to the specific receptor is the europium cryptate Eu tris-bipyridine or the terbium cryptate Tb tris-bipyridine.

16. The method according to claim 1, wherein the specific receptors are selected from polyclonal and monoclonal antibodies.

17. A kit for detecting and/or determining the phosphorylating activity of a biological material towards a substrate containing tyrosine and/or serine and/or threonine, comprising at least one carrier molecule including a luminescent molecule or a non-luminescent molecule bonded to at least one luminescent marker or at least one emission signal modulator, to which a plurality of identical or different peptides or polypeptides containing tyrosine and/or serine and/or threonine are covalently fixed, and at least one specific receptor for said phosphorylated peptides or polypeptides, said receptor being bonded to at least one luminescent marker or at least one emission signal modulator.

18. A kit according to claim 17, wherein the carrier molecule and the luminescent marker molecule bonded to the specific receptor are fluorescent molecules.

19. A kit according to claim 18, wherein the luminescent marker or the emission signal modulator bonded to the specific receptor, and the carrier molecule, are respectively fluorescent donor and acceptor molecules.

20. A kit according to claim 17, wherein the luminescent compound bonded to the specific receptor is the europium cryptate Eu tris-bipyridine or the terbium cryptate Tb tris-bipyridine.

21. A kit according to claim 17, wherein said kit contains an appropriate buffer medium, and a source of non-radiolabeled phosphate and instructions for carrying out the method according to any one of claims 1 to 16.

* * * * *